United States Patent
Steger et al.

(10) Patent No.: US 10,675,107 B2
(45) Date of Patent: Jun. 9, 2020

(54) SURGICAL INSTRUMENT END EFFECTOR WITH INTEGRAL FBG

(71) Applicant: Intuitive Surgical Operations, Inc., Sunnyvale, CA (US)

(72) Inventors: John Ryan Steger, Sunnyvale, CA (US); Grant M. Kadokura, San Diego, CA (US); Andrew C. Waterbury, Sunnyvale, CA (US); Manuel Ahumada, San Jose, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 0 days.

(21) Appl. No.: 16/192,475

(22) Filed: Nov. 15, 2018

(65) Prior Publication Data

US 2019/0142536 A1 May 16, 2019

Related U.S. Application Data

(60) Provisional application No. 62/586,729, filed on Nov. 15, 2017.

(51) Int. Cl.
| | | |
|---|---|---|
| A61B 34/35 | (2016.01) | |
| A61B 34/00 | (2016.01) | |
| A61B 17/00 | (2006.01) | |
| A61B 34/30 | (2016.01) | |
| A61B 34/20 | (2016.01) | |
| A61B 90/00 | (2016.01) | |
| A61B 34/37 | (2016.01) | |

(52) U.S. Cl.
CPC .............. *A61B 34/35* (2016.02); *A61B 34/20* (2016.02); *A61B 34/71* (2016.02); *A61B 34/76* (2016.02); *A61B 90/361* (2016.02); *A61B 34/37* (2016.02); *A61B 90/37* (2016.02); *A61B 2017/00389* (2013.01); *A61B 2017/00477* (2013.01); *A61B 2034/2061* (2016.02); *A61B 2034/305* (2016.02); *A61B 2090/065* (2016.02); *A61B 2090/3614* (2016.02)

(58) Field of Classification Search
CPC ....................................................... A61B 34/35
See application file for complete search history.

(56) References Cited

U.S. PATENT DOCUMENTS

| | | | |
|---|---|---|---|
| 8,622,935 B1* | 1/2014 | Leo ....................... | A61B 5/6843 600/587 |
| 9,113,904 B2* | 8/2015 | Kerr .................... | A61B 18/1445 |
| 2015/0135832 A1* | 5/2015 | Blumenkranz ....... | G01P 15/093 73/514.26 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

*Primary Examiner* — Omar R Rojas
(74) *Attorney, Agent, or Firm* — Schwegman, Lundberg & Woessner, P.A.

(57) ABSTRACT

A surgical instrument is provided that includes an elongated shaft that includes a proximal end and a distal end; a cantilever beam is disposed at the distal end of the shaft; an optical fiber extends within a channel that extends within between proximal and distal portions of the cantilever beam; a first fiber Bragg grating (FBG) is formed in a segment of the optical fiber within the proximal portion of the beam; a second FBG is formed in a segment of the optical fiber within the distal portion of the beam.

12 Claims, 9 Drawing Sheets

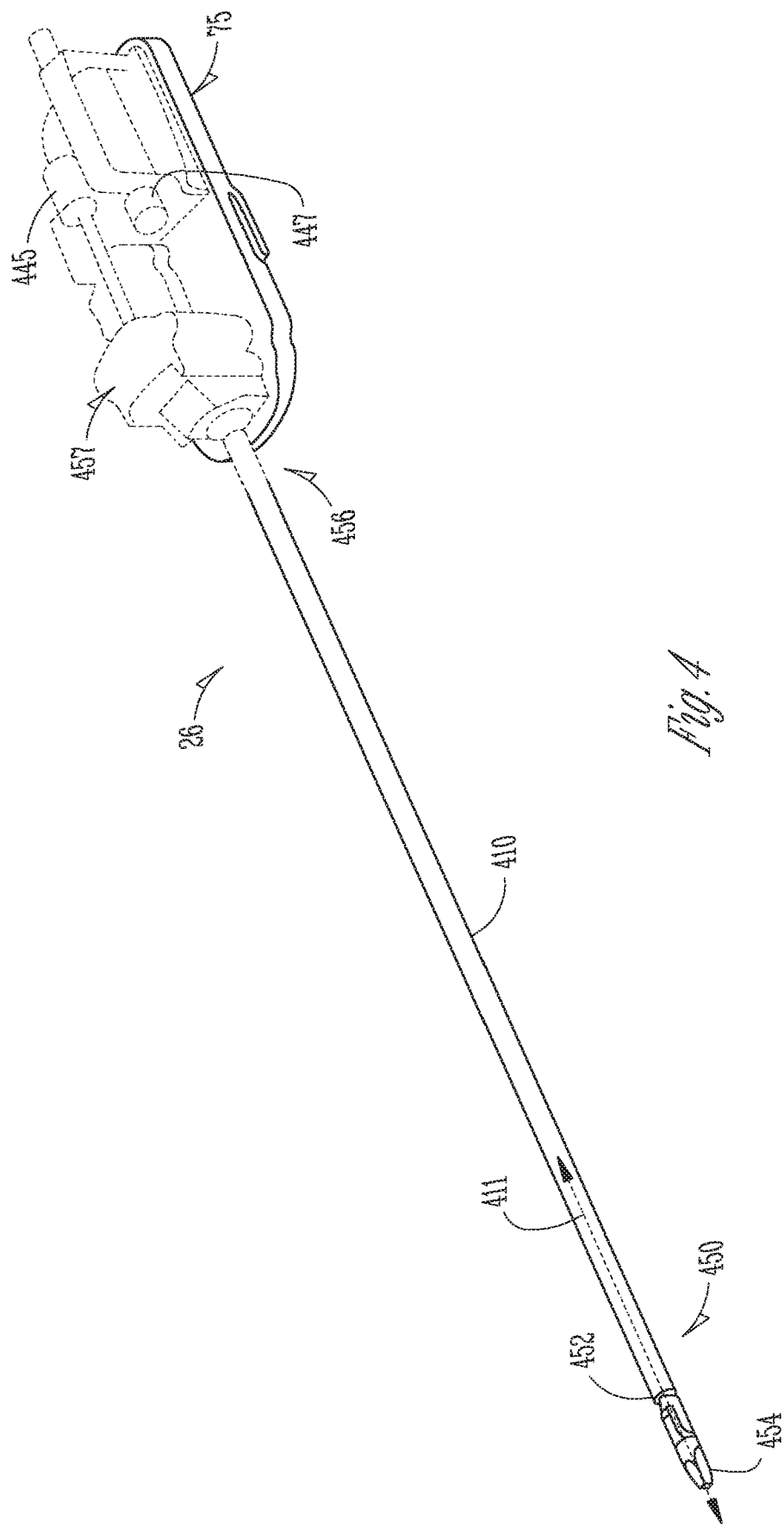

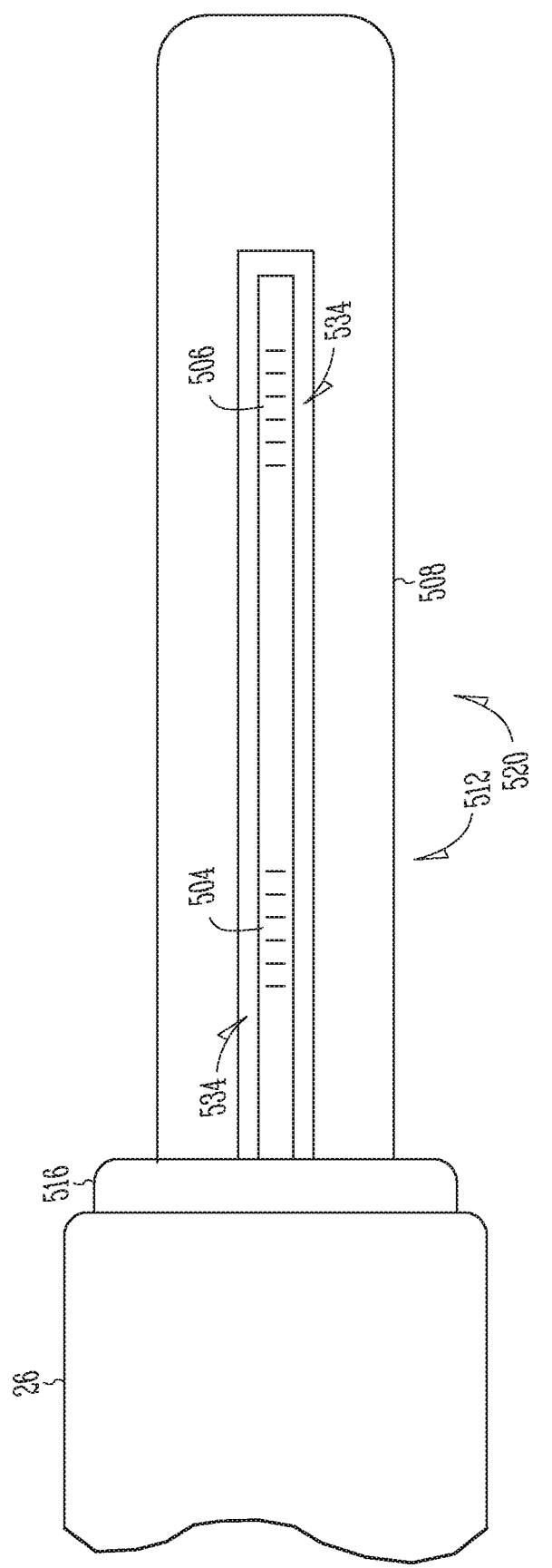

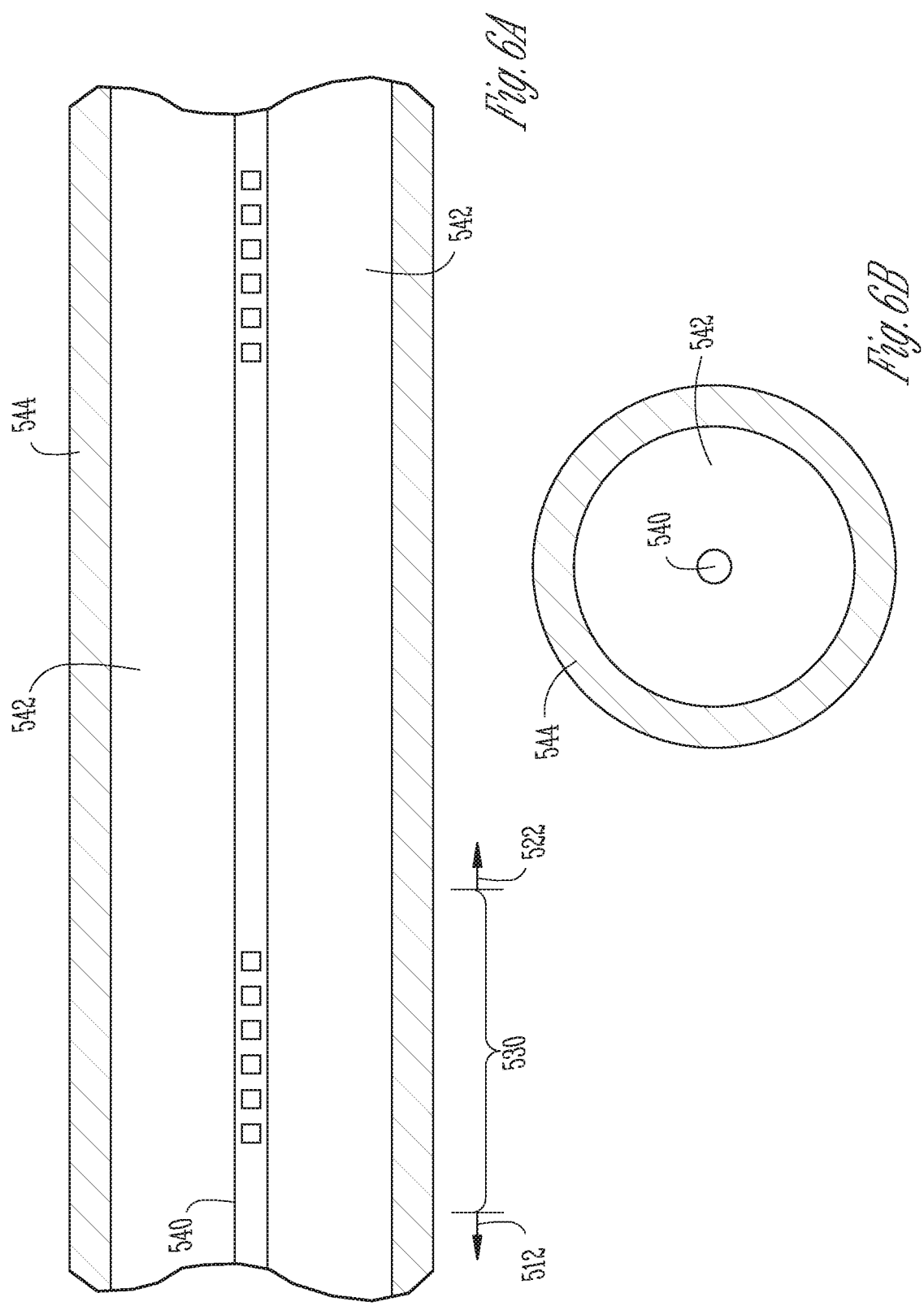

SURGICAL INSTRUMENT END EFFECTOR WITH INTEGRAL FBG

CLAIM OF PRIORITY

This application claims the benefit of priority under 35 U.S.C. § 119(e) to U.S. Provisional Patent Application Ser. No. 62/586,729, filed on Nov. 15, 2017, each of which is incorporated by reference herein in its entirety.

BACKGROUND

Minimally invasive medical techniques are intended to reduce the amount of tissue that is damaged during diagnostic or surgical procedures, thereby reducing patient recovery time, discomfort, and deleterious side effects. Teleoperated surgical systems that use robotic technology (so-called surgical robotic systems) may be used to overcome limitations of manual laparascopic and open surgery. Advances in telepresence systems provide surgeons views inside a patient's body, an increased number of degrees of motion of surgical instruments, and the ability for surgical collaboration over long distances. In manual minimally invasive surgery, surgeons feel the interaction of the instrument with the patient via a long shaft, which eliminates tactile cues and masks force cues. In teleoperation surgery systems, natural force feedback is largely eliminated because the surgeon no longer manipulates the instrument directly. Kinesthetic or force feedback systems typically measure or estimate the forces applied to the patient by the surgical instrument.

SUMMARY

In one aspect, a surgical instrument is provided that includes an elongated shaft that includes a proximal end and a distal end. A cantilever beam is disposed at the distal end of the shaft. An optical fiber extends within a channel that extends within between proximal and distal portions of the cantilever beam. A first fiber Bragg grating (FBG) is formed in a segment of the optical fiber within the proximal portion of the beam. A second FBG is formed in a segment of the optical fiber within the distal portion of the beam.

In another aspect, a surgical instrument is provided that includes an elongated shaft that includes a proximal end and a distal end. A support base member is secured to the distal end of the shaft. First and second force-sensing cantilever beams are secured to the support base member. A center cantilever beam is secured to the support base member between the first and second force-sensing beams. A first optical fiber including a first fiber Bragg grating (FBG) is disposed upon the first force-sensing beam. A second optical fiber including a second FBG is disposed upon the second force-sensing beam.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 4 is a perspective view of a surgical instrument used with the minimally invasive teleoperated surgical system of FIG. 1.

FIG. 5B is a cross-sectional top view of the first cantilever beam of FIG. 5A.

FIG. 6A is a side cross section view of a portion of the optical fiber of FIGS. 5A-5B.

FIG. 6B is an end cross-section view of the optical fiber 536 of FIGS. 5A-5B.

DESCRIPTION OF EMBODIMENTS

Teleoperated Surgical System

Figure 1:
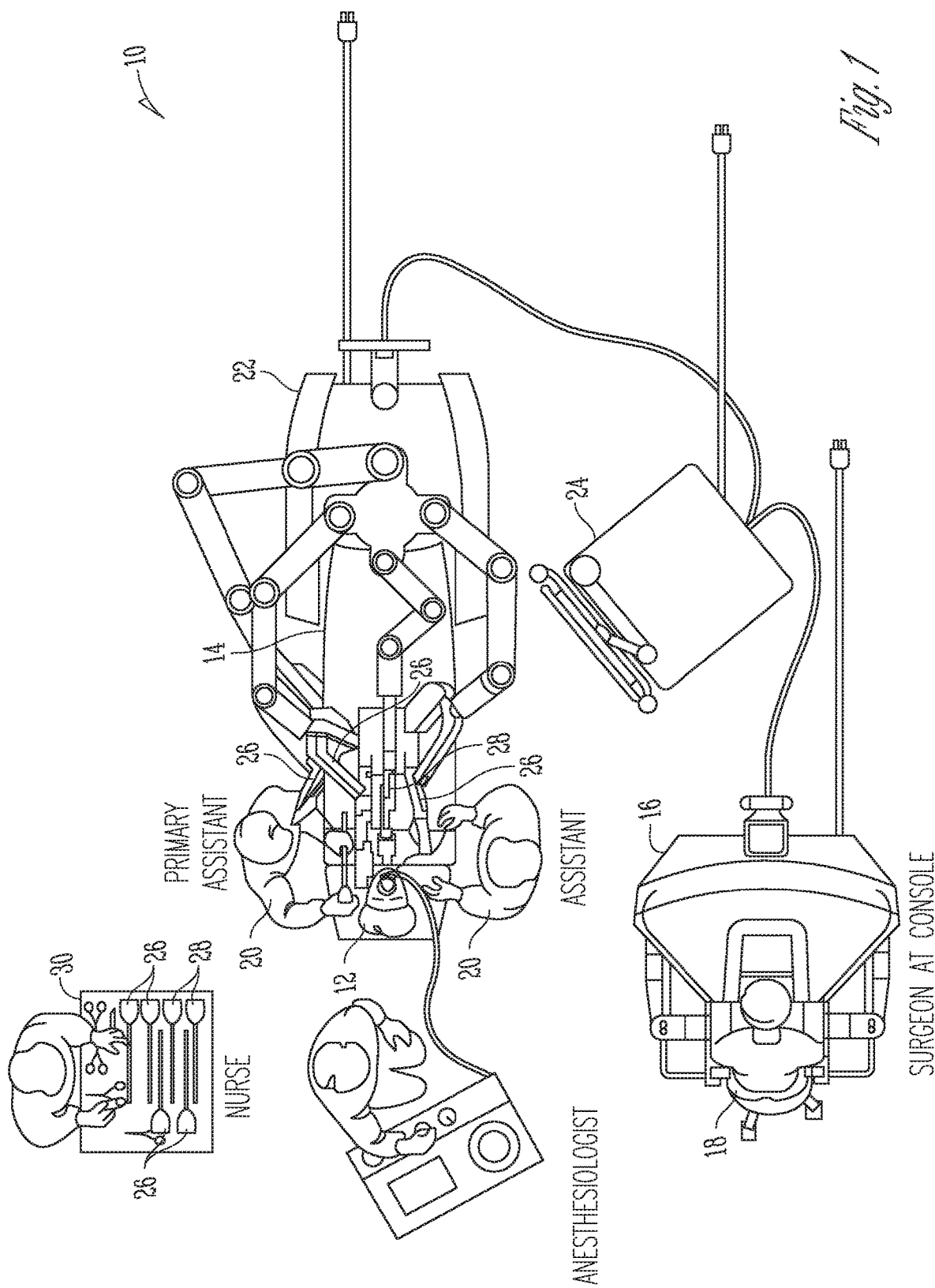
FIG. 1 is an illustrative plan view of a minimally invasive teleoperated surgical system.

FIG. 1 is an illustrative plan view of a minimally invasive teleoperated surgical system 10 for performing a minimally invasive diagnostic or surgical procedure on a patient 12 who is lying on an operating table 14. The system includes a surgeon's console 16 for use by a surgeon 18 during the procedure. One or more assistants 20 may also participate in the procedure. The minimally invasive teleoperated surgical system 10 further includes a patient-side cart 22 and an electronics cart 24. The patient-side cart 22 can manipulate at least one surgical instrument 26 through a minimally invasive incision in the body of the patient 12 while the surgeon 18 views the surgical site through the surgeon's console 16. An image of the surgical site can be obtained by an endoscope 28, such as a stereoscopic endoscope, which may be manipulated by the patient-side cart 22 to orient the endoscope 28. Computer processors located on the electronics cart 24 may be used to process the images of the surgical site for subsequent display to the surgeon 18 through the surgeon's console 16. In some embodiments, stereoscopic images may be captured, which allow the perception of depth during a surgical procedure. The number of surgical instruments 26 used at one time will generally depend on the diagnostic or surgical procedure and the space constraints within the operative site among other factors. If it is necessary to change one or more of the surgical instruments 26 being used during a procedure, an assistant 20 may remove the surgical instrument 26 from the patient-side cart 22, and replace it with another surgical instrument 26 from a tray 30 in the operating room.

Figure 2:
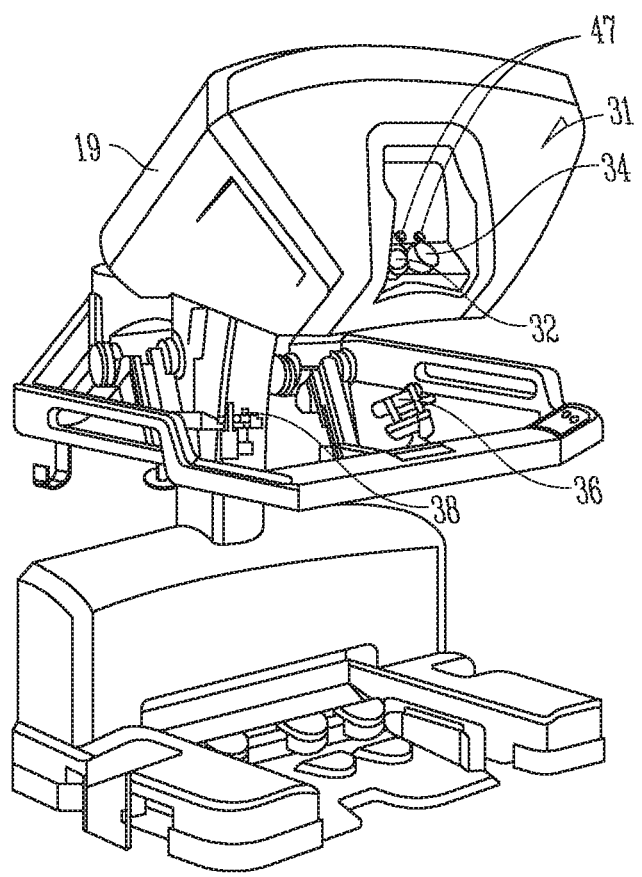
FIG. 2 is a perspective view of the surgeon's console of the minimally invasive teleoperated surgical system of FIG. 1.

FIG. 2 is a perspective view of the surgeon's console 16. The surgeon's console 16 includes a viewer display 31 that includes a left eye display 32 and a right eye display 34 for presenting the surgeon 18 with a coordinated stereoscopic view of the surgical site that enables depth perception. The console 16 further includes one or more hand-operated control inputs 36 to receive the larger-scale hand control movements. One or more surgical instruments installed for use on the patient-side cart 22 move in smaller-scale distances in response to surgeon 18's larger-scale manipulation of the one or more control inputs 36. The control inputs 36 may provide the same mechanical degrees of freedom as their associated surgical instruments 26 to provide the surgeon 18 with telepresence, or the perception that the control inputs 36 are integral with the instruments 26 so that the surgeon has a strong sense of directly controlling the instruments 26. To this end, position, force, and tactile feedback sensors (not shown) may be employed to transmit position, force, and tactile sensations from the surgical instruments 26 back to the surgeon's hands through the control inputs 36, subject to communication delay constraints.

Figure 3:
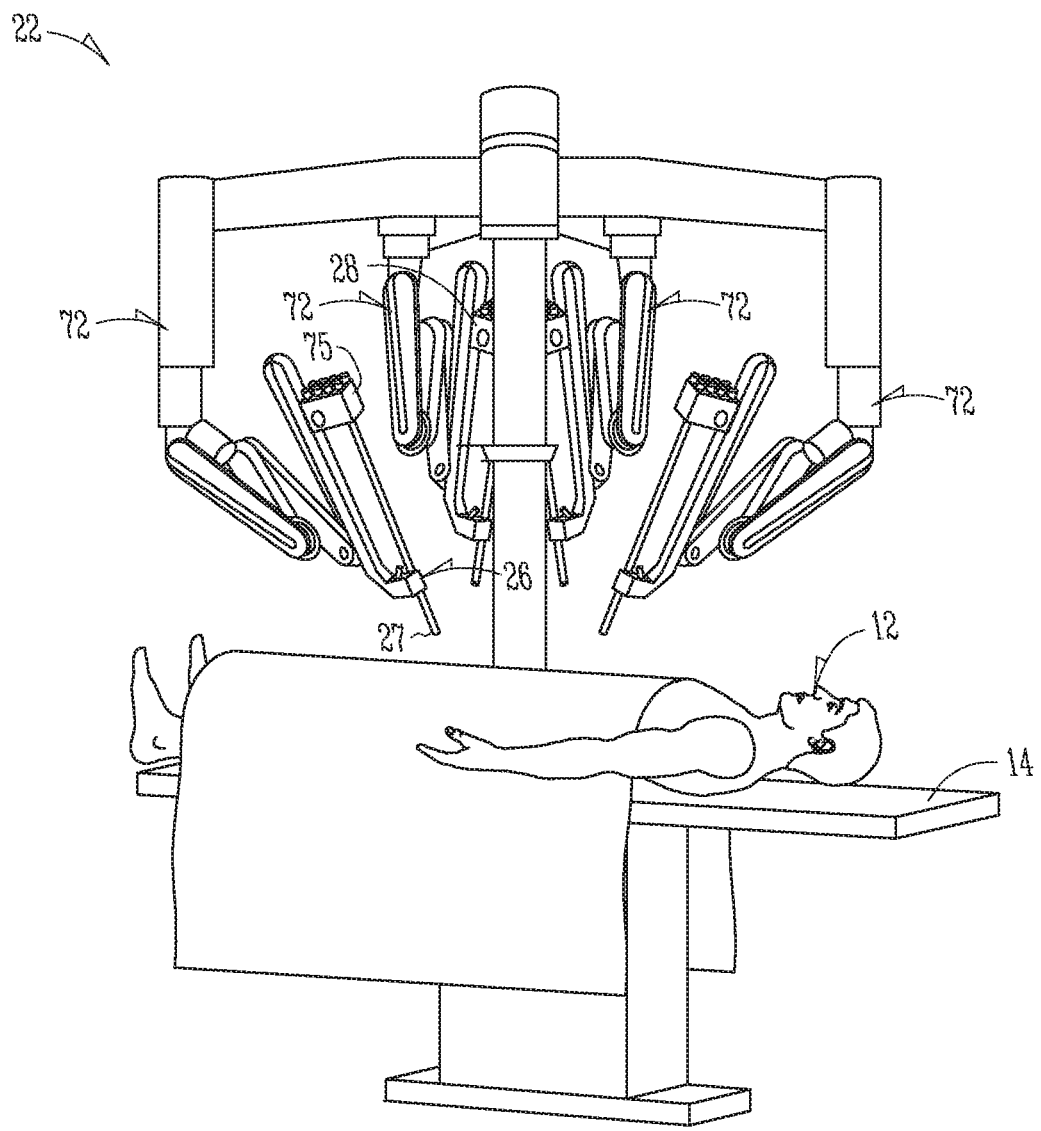
FIG. 3 is a perspective view of a patient-side cart of a minimally invasive teleoperated surgical system of FIG. 1.

FIG. 3 is a perspective view of a patient-side cart 22 of a minimally invasive teleoperated surgical system 10, in accordance with embodiments. The patient-side cart 22 includes four mechanical support arms 72. A surgical instrument manipulator 73, which includes motors to control instrument motion, is mounted at the end of each support arm assembly 72. Additionally, each support arm 72 can optionally include one or more setup joints (e.g., unpowered and/or lockable) that are used to position the attached surgical instrument manipulator 73 in relation to the patient for surgery. While the patient-side cart 22 is shown as including four surgical instrument manipulators 73, more or fewer surgical instrument manipulators 73 may be used. A teleoperated surgical system will generally include a vision system that typically includes a endoscopic camera instrument 28 for capturing video images and one or more video displays for displaying the captured video images.

In one aspect, for example, individual surgical instruments 26 and a cannulas 27 are removably coupled to manipulator 73, with the surgical instrument 26 inserted through the cannula 27. One or more teleoperated actuator motors of the manipulator 73 move the surgical instrument 26 as a whole. The manipulator 73 further includes an instrument carriage 75. The surgical instrument 26 is detachably connected to the instrument carriage 75. In one aspect, the instrument carriage 75 houses one or more teleoperated actuator motors (not shown) inside that provide a number of controller motions that the surgical instrument 26 translates into a variety of movements of an end effector on the surgical instrument 26. Thus, the teleoperated actuator motors within the instrument carriage 75 may selectably move only one or more components of the surgical instrument 26 rather than the instrument as a whole. Inputs to control either the instrument as a whole or the instrument's components are such that the input provided by a surgeon or other medical person to the control input (a "master" command) is translated into a corresponding action by the surgical instrument (a "slave" response). A wire cable-based force transmission mechanism or the like is used to transfer the motions of each of the remotely located teleoperated actuator motors to a corresponding instrument-interfacing actuator output located on instrument carriage 75. In some embodiments, the surgical instrument 26 is mechanically coupled to a first actuator motor, which controls a first motion of the surgical instrument such as longitudinal (z-axis) rotation. The surgical instrument 26 is mechanically coupled to a second actuator, which controls second motion of the surgical instrument such as two-dimensional (x, y) motion. The surgical instrument 26 is mechanically coupled to a third actuator, which controls third motion of the surgical instrument such as opening and closing of jaws of an end effector, for example.

FIG. 4 is a perspective view of a surgical instrument 26, which includes an elongated hollow tubular shaft 410 having a centerline longitudinal axis 411, a distal (first) end portion 450 for insertion into a patient's body cavity and proximal (second) end portion 456 that includes a wire coupling mechanism 457, which may include one or more pulleys, guides or anchors, to operatively mechanically couple wires to one or more motors 445, 447 (shown with dashed lines), within an instrument carriage 75, to exert force upon wire cables (not shown). The wires are operatively coupled so that movement of the wires may impart motion to an end effector such as opening or closing of jaws, two-dimensional (x, y) motion and longitudinal (z-axis) rotation, for example. The surgical instrument 26 may be used to carry out surgical or diagnostic procedures. The distal portion 450 of the surgical instrument 26 can provide any of a variety of end effectors 454, such as the forceps shown, a needle driver, a cautery device, a cutting tool, an imaging device (e.g., an endoscope or ultrasound probe), or the like. The surgical end effector 454 can include a functional mechanical degree of freedom, such as jaws that open or close, or a knife that translates along a path or a wrist that may move in two-dimensional x and y directions and that may rotate about a longitudinal z-axis. In the embodiment shown, the end effector 454 is coupled to the elongated hollow shaft 410 by a wrist 452 that allows the end effector to be oriented relative to the elongate tube centerline axis 411. The control mechanism 440 controls movement of the overall instrument and the end effector at its distal portion.

Cantilever Beam End Effector with FBGs within Thin Proximal Portion

Figure 5A:
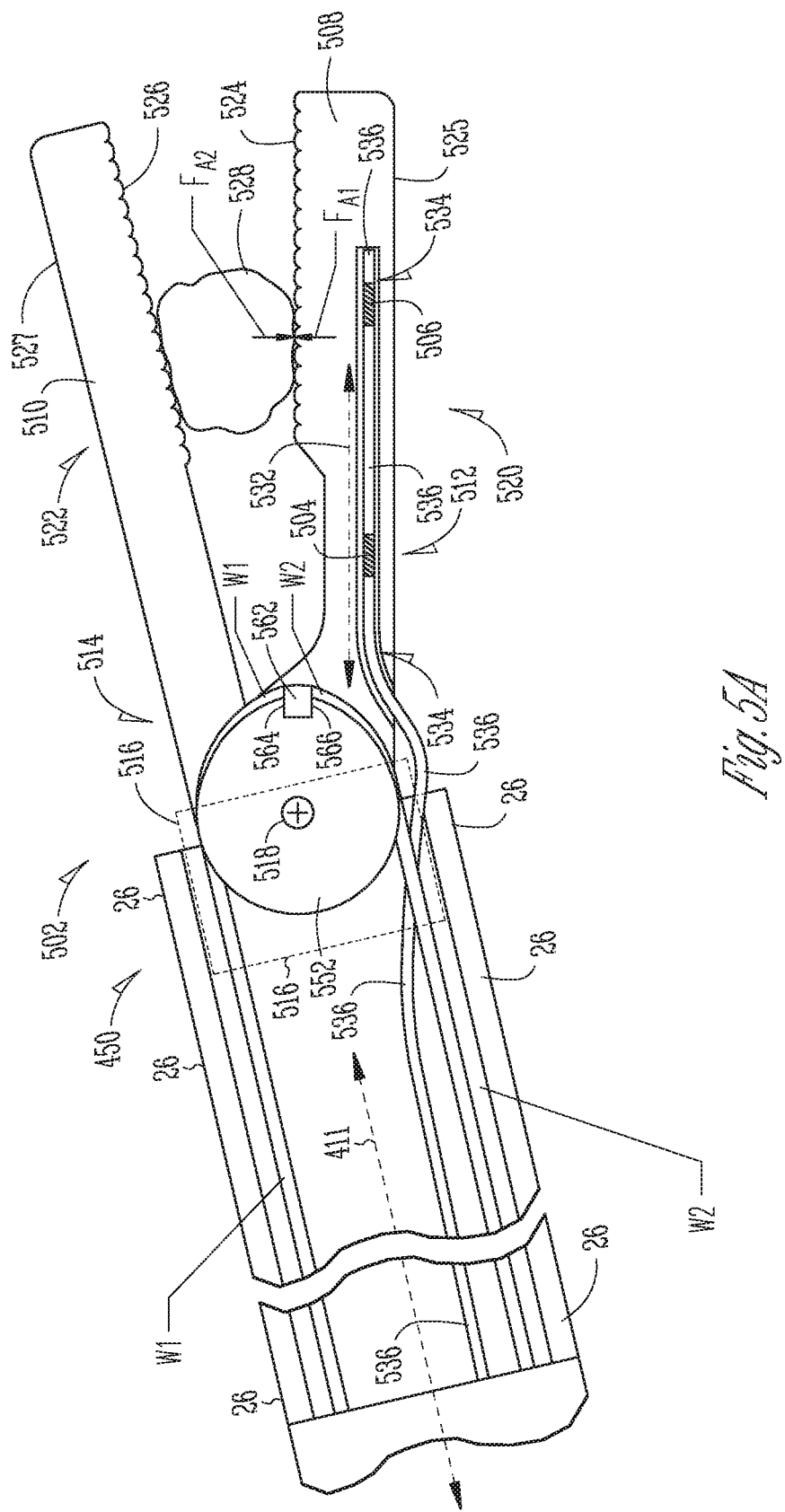
FIG. 5A is an illustrative cross-sectional side view of a first embodiment of a surgical instrument end effector having integral fiber Bragg gratings (FBGs).

FIG. 5A is an illustrative cross-sectional side view of a first embodiment of a surgical instrument end effector 502 having integral first and second fiber Bragg gratings (FBGs) 504, 506. The end effector 502 depends from a distal end portion 450 of a surgical instrument shaft 26. More specifically, the first embodiment end effector 502 includes first and second cantilever beams 508, 510, which act as first and second jaws, having respective proximal portions 512, 514 secured to a support base member 516 (indicated by dashed lines) at the distal end portion 450 of the shaft 26. The proximal portion 512 of the second cantilever beam 510 is fixedly secured to extend longitudinally from the support base member 516. The proximal portion 514 of the first cantilever beam 508 is mounted to pivot about a pivot axis 518 that extends transversely through the support base member 516. The first cantilever beam 508 may be selectably rotated about the pivot axis 518 in a direction away the second cantilever beam 510 to an open jaw position in which the first and second cantilever beams 508, 510 act as a pair of opened jaws. Alternatively, the first cantilever beam 508 may be selectably rotated in a direction toward the second cantilever beam 510 to a closed jaw position in which the first and second cantilever beams 508, 510 act as a pair of closed jaws. The first and second cantilever beams 508, 510 include respective second distal portions 520, 522 that include respective first and second opposed facing working face surfaces 524, 526 and back face surface 525, 527. The working face surfaces 524, 526 may be textured to contact and grip anatomical tissue 528 between them when the first cantilever beam 508 is rotationally positioned to capture the tissue 528 between the first and second cantilever beams 508, 510.

FIG. 5B is a cross-sectional top view of the first cantilever beam of FIG. 5A. Referring to FIGS. 5A-5B, the proximal portion 512 of the first cantilever beam 508 disposed between the first cantilever beam 508 includes a neutral axis 532 that extends longitudinally within the proximal portions 512. The neutral axis 532 is at the midpoint of the beam 508 during bending where there is no strain due to bending. The first cantilever beam 508 defines a channel 534 that extends within its proximal portion 512 and within its distal portion 520. A first portion of the channel 534 that extends within the proximal portion 512 extends parallel to the neutral axis 532 and is offset from the neutral axis 532. In some embodiments, the channel 534 may include a circular cross-section bore hole.

An optical fiber 536 extends within the hollow shaft 26 and within the channel 534. The optical fiber 536 is disposed away from the midpoint so as to experience strain during bending of the beam 508. The first FBGs 504 are formed in a first segment of the optical fiber 536 disposed within the first portion of the channel 534 within the proximal portion 512 of the first cantilever beam 508, to detect a change in reflected light wavelength due to bending strain imparted to the proximal portion 512. The second FBGs 506 are formed in a second segment of the optical fiber 536 disposed within a second portion of the channel 534 within the distal portion 520 of the first cantilever beam 508 at a location isolated from bending strain imparted to the proximal portion 512, to detect a change in reflected light wavelength due to temperature. A filler material (not shown) such as an epoxy is inserted within the channel 534 to fill a space between the optical fiber 536 and walls of the channel 534. The filler acts to transfer strain from the walls of the channel 534 to the first FBGs 504 formed within the optical fiber 536.

FIG. 6A is a side cross section view of a portion of the optical fiber 536 of FIGS. 5A-5B. FIG. 6B is an end cross-section view of the optical fiber 536 of FIGS. 5A-5B. The optical fiber 536 is formed from a glass material and includes a transparent core 540 surrounded by a transparent cladding material 542 with a lower index of refraction. The difference of refraction indexes between the inner core 540 and the cladding 542 causes light to propagate only inside the inner core 540. The optical fiber 536 also may include a protective outer buffer layer 544 such as an acrylic or polyimide material to protect against water and hydrogen which otherwise may promote crack growing and reduce mechanical stability.

The first and second FBGs 504, 506 are formed in the inner core 540. The first FBGs 504 are formed in a segment of the core 540 disposed in the first cantilever beam's proximal portion 512. The second FBGs 506 are formed in a segment of the core 540 disposed in the first cantilever beam's distal portion 520.

When broad spectrum light beam is sent to an FBG, such as either one of the first and second FBGs 504, 506, the FBG reflects a specific frequency of light and transmits all others as described by equation (1).

$$\lambda_b = 2n\Lambda \quad (1)$$

In the above equation, $\lambda_b$ is the Bragg wavelength, n is the effective refractive index of the fiber core, and $\Lambda$ is the spacing between the gratings, known as the grating period.

Changes in strain and temperature affect both the effective refractive index n and grating period $\Lambda$ of an FBG, which results in a shift in the reflected wavelength. Thus, an FBG reflects a wavelength of light that shifts in response to variations in temperature and/or strain. The change of wavelength of an FBG due to strain and temperature can be approximately described by equation (2):

$$\Delta\lambda/\lambda_O = (1-p_e)*\varepsilon + (\alpha_\Lambda + \alpha_n)*\Delta T \quad (2)$$

where $\Delta\lambda$ is the wavelength shift and $\lambda_O$ is the initial wavelength. The first expression describes the impact of strain on the wavelength shift, where $p_e$ is the strain-optic coefficient, and $\varepsilon$ is the strain experienced by the grating. The second expression describes the impact of temperature on the wavelength shift, where $\alpha_\Lambda$ is the thermal expansion coefficient and an is the thermo-optic coefficient. The value $\alpha_n$ describes the change in refractive index while $\alpha_\Lambda$ describes the expansion of the grating, both due to temperature.

Referring again to FIG. 5A, during a surgical procedure, for example, a position of the first cantilever beam proximal portion 512 may be secured in a rotationally fixed position to the support base member 516 at the distal end of the shaft 26 while a surgeon manipulates the first cantilever beam 508 its working face surface 524 imparts a first direction force $F_{A1}$ upon the anatomical tissue 528. Specifically, for example, the surgeon may cause the first cantilever beam 508 to rotate toward the second cantilever beam 510 to squeeze the tissue 528 between them. The anatomical tissue 528, in turn, may exert a second opposite-direction counter-force $F_{A2}$ upon the first cantilever beam working face surface 524 to resist the first force $F_{A1}$. The first and second forces act in opposite directions that each is generally perpendicular to the neutral axis 532 of the first cantilever beam's proximal portion 512. The second force $F_{A2}$ may impart a bending strain to the proximal portion 512 that is imparted to the first FBGs 504 disposed within the proximal portion 512.

The first cantilever beam's proximal portion 512 has a transverse thickness, between the working face 524 and the back face 525, that is sufficiently smaller than that of the first cantilever beam's distal portion 520 that the second force $F_{A2}$ imparted to the first cantilever beam working surface 524 imparts greater bending strain to the first FBGs 504 within the proximal portion 512 than it imparts to the second FBGs 506 within the distal portion 520. In some embodiments, the proximal portion 512 is thin enough that the second force $F_{A1}$ may impart a strain to the first FBGs 504 that causes in a shift in reflected wavelength. In some embodiments, the distal portion 520 is thick enough to isolate the second FBGs 506 from the second force $F_{A2}$ such that little or no strain is imparted to the second FBGs 506. In some embodiments, the cantilever beam 508 is formed of a metal material that has a high coefficient of thermal conductivity. The second FBGs 506, which do not experience strain during bending of the beam 508, are used to compensate for the impact of temperature shifts upon reflected light wavelength shifts the first FBGs 504, which do experience strain during bending of the beam 508.

More particularly, the first cantilever beam's proximal portion 512 is thin enough that strain upon the first FBGs 504 due to a typical second force $F_{A2}$ having a typical magnitude is large enough to have an impact upon reflected wavelength shift of the first FBGs 504. Conversely, the first cantilever beam's distal portion 520 is thick enough that strain upon the second FBGs 506 caused due to a typical second force $F_{A2}$ with a typical magnitude is small enough to have a negligible impact upon reflected wavelength shift of the second FBGs 506. In some embodiments, the second force $F_{A2}$ has a typical magnitude in a range 0-2 newtons.

Thus, a bending stress imparted to the first cantilever beam's proximal portion 512 is transferred to the first FBGs 504 causes a shift in wavelength reflected by the first FBGs 504 that is indicative of the magnitude of the bending strain imparted to the proximal portion 512. As explained by equation (2), the wavelength of the light reflected by the first FBGs 504 varies with both strain and temperature. Since the second FBGs 506 disposed within the distal portion 520 are isolated from strain imparted to the proximal portion 512, the light reflected by the second FBGs 506 varies only with temperature. Since when in use the first and second FBGs 504, 506 have identical temperatures, the light wavelength reflected by the second FBGs 506 may be used for temperature calibration of the first FBGs 504 to determine a temperature independent shift in reflected light wavelength of the first FBGs 504 caused by strain in the first cantilever beam's proximal portion 512. A magnitude of the second force $F_{A2}$ may be determined based upon the temperature independent shift in reflected light wavelength of the first FBGs 504.

Still referring to FIG. 5A, the support base member 516 includes a pulley 552 that is rotatably mounted between arms of a clevis (not shown) disposed at the distal end of the shaft 26 for rotation about the pivot axis 518. The first cantilever beam proximal portion 512 is integrally formed with the pulley 552. First and second wires W1, W2 extend within the shaft 26 to control rotational position of the base pulley 552, and of the first cantilever beam 508, about the pivot axis 518. During a surgical procedure, for example, tension forces may be imparted to each of the first and second wires W1, W2 to maintain a fixed rotational position of the pulley 552 and the cantilever beam 508 depending therefrom. A wire anchor structure 562 secured to a side face of the first cantilever beam 508. A distal end of the first wire W1 is secured to a first side 564 of the anchor 562 and extends within a circumferential groove (not shown) in an outer edge of the pulley 552 between the first side 764 and the shaft 26. A distal end of the second wire W2 is secured to a second side 566 of the anchor 562 and extends wraps about a portion of the pulley 552 within a circumferential groove (not shown) in an outer edge of the pulley 552 between the second side 566 of the anchor 562 and the shaft 26.

Referring to FIG. 4 and to FIG. 5A, a first actuator motor M1 may impart a first proximal direction force upon the first wire W1 coupled to the anchor's first side 564 to rotate the pulley 552 in a second (counter-clockwise) direction. A second actuator motor M2 may impart a second proximal direction force upon the second wire W2 coupled to the anchor's second side 566 to rotate the pulley in a second (clockwise) rotation. The first and second motors M1, M2 may impart proximal direction forces in unison to temporarily hold the pulley 552 and the cantilever beam 508 in a fixed position.

Cantilever Beam End Effector with Integral FBGs within Tapered Contour

Figure 7:
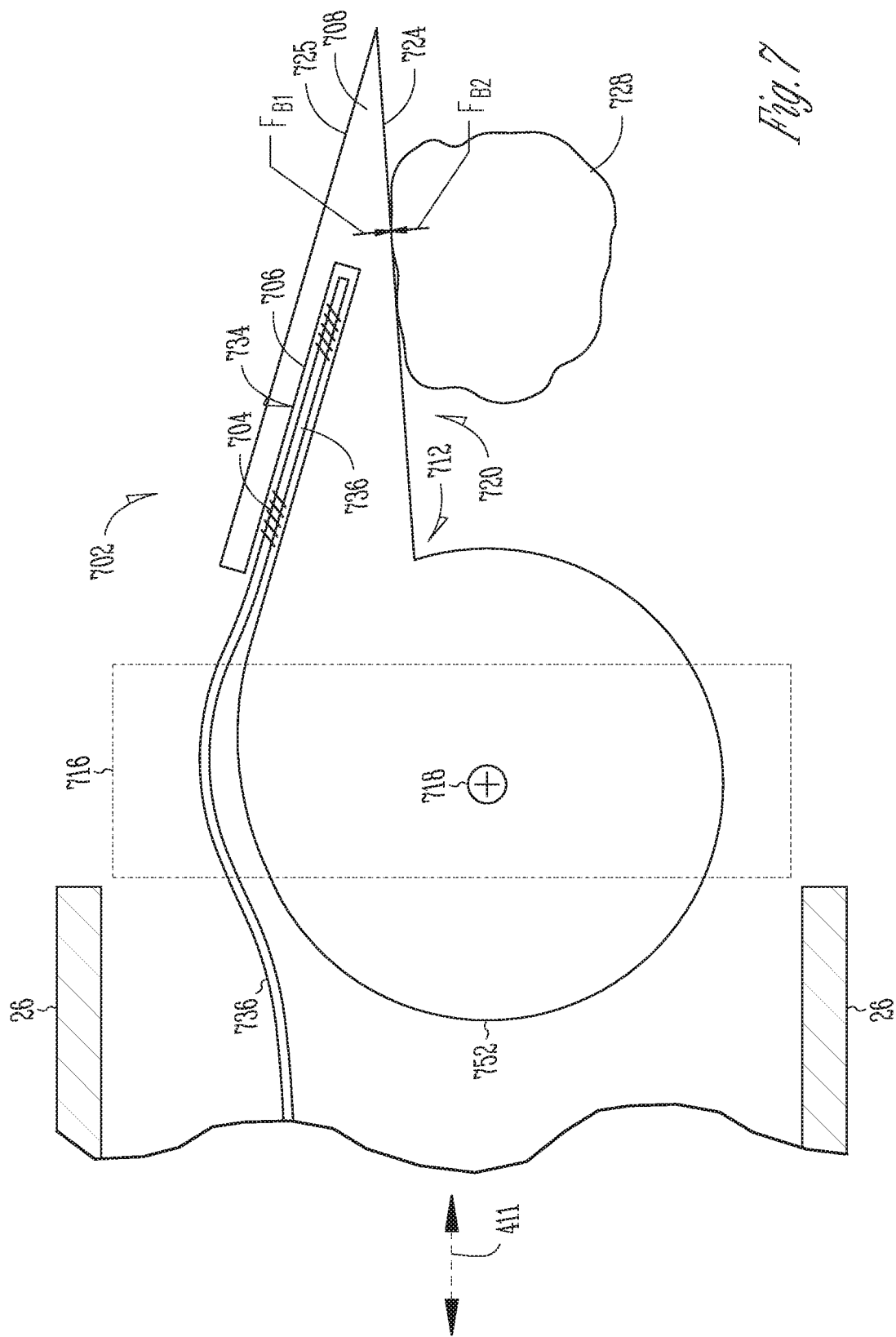
FIG. 7 is an illustrative cross-sectional partially transparent side view of a second embodiment of a surgical instrument end effector having integral FBGs.

FIG. 7 is an illustrative cross-sectional side view of a second embodiment of a surgical instrument end effector 702 having integral first and second FBGs 706, 704. The end effector 702 depends from a distal end portion 450 of a surgical instrument shaft 26. The end effector includes a cantilever beam 708 having a working face surface 724 to contact anatomical tissue 728 and a back face 725. The cantilever beam 708 includes a cantilever beam proximal portion 712 and a cantilever beam distal portion 720. The cantilever beam proximal portion 712 is integrally coupled to a support base member 716, indicated by dashed lines, secured to the distal end a surgical instrument shaft 26. In some embodiments, the cantilever beam proximal portion 712 support is integrally secured to a base pulley 752 that is rotatably mounted between arms of a clevis (not shown) disposed at the distal end of the shaft 26 for rotation about a pivot axis 756. The cantilever beam proximal portion 712 has greater thickness than the cantilever beam distal portion 720. In some embodiments, a thickness of the cantilever beam 708 tapers from being thicker at a cantilever beam base portion 712 where the cantilever beam proximal portion 712 is secured to the distal end of the shaft 26 to being thinner at the cantilever beam distal portion 720.

The cantilever beam 708 defines a channel 734 that extends between the thicker cantilever beam proximal portion 712 and the thinner cantilever beam distal portion 720. In some embodiments, the channel may include circular cross-section bore hole. An optical fiber 736 extends within the channel 734. The first FBGs are formed in a segment of the optical fiber 736 disposed within the thinner distal portion 720 of the cantilever beam 708 to detect changes in reflected light wavelength caused by bending strain imparted to the distal portion 720. The second FBGs 704 are formed in a segment of the optical fiber 736 disposed within the thicker proximal portion 720 of the cantilever beam 708 at a location isolated from bending strain imparted to the distal portion 720, to detect changes in reflected light wavelength caused by temperature changes. A filler material 738 is inserted within the channel 734 to transfer strain between the walls of the channel 734 and the first FBGs 706.

During a surgical procedure, for example, a rotational position of the base pulley 752 and the proximal cantilever beam portion 712 may be temporarily fixed in relation to a longitudinal axis 411 of the shaft 26 while a surgeon manipulates the cantilever beam 708 to impart a first direction force $F_{B1}$ upon the anatomical tissue 728. The anatomical tissue 728, in turn, may exert a second opposite-direction counter-force $F_{B2}$ upon the working face surface 724 to resist the first force $F_{B1}$. The second force $F_{B2}$ imparted by the anatomical tissue, for example, causes a bending stress at the first FBGs 706 disposed within the distal portion 720 of the cantilever beam 708. From the discussion above, a person skilled in the art will understand the use of wires to control rotation of the pulley 752.

The distal portion 720 of the cantilever beam 708 has a cross section thickness that is sufficiently smaller than that of the proximal portion 712 of the cantilever beam 708 that the second force $F_{B2}$ imparted to the working face surface 724 imparts greater bending strain to the first FBGs 706 within a portion of the channel 734 within the distal portion 720 than it imparts to the second FBGs 704 disposed within the portion of the channel 734 within the proximal portion 712. In some embodiments, the cantilever beam distal portion 720 is thin enough that the second force $F_{A2}$ may impart a strain to the first FBGs 706 that causes in a shift in reflected wavelength. In some embodiments, the cantilever beam proximal portion 712 is thick enough to isolate the second FBGs 704 from the second force $F_{B2}$ such that little or no strain is imparted to the second FBGs.

More particularly, the distal portion 720 of the cantilever beam 708 is thin enough that strain upon the first FBGs 706 due to a typical second force $F_{B2}$ having a typical magnitude is large enough to have an impact upon reflected wavelength shift of the first FBGs 706. Conversely, the proximal portion 712 of the cantilever beam 708 is thick enough that strain upon the second FBGs 704 caused due to a typical second force $F_{B2}$ with a typical magnitude is small enough to have a negligible impact upon reflected wavelength shift of the second FBGs 704.

Center Cantilever Beam End Effector Between Cantilever Beams with Integral FBGs

Figure 8:
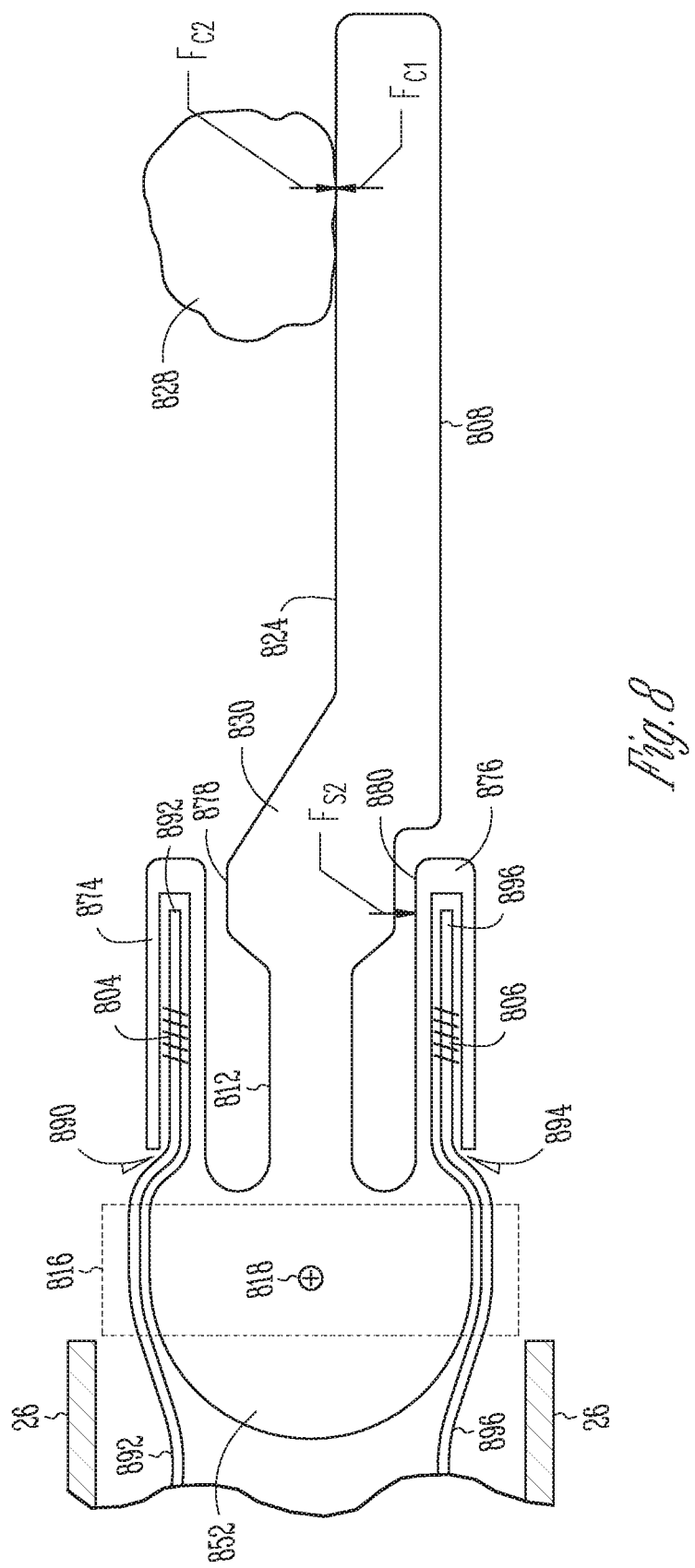
FIG. 8 is an illustrative cross-sectional side view of a third embodiment of a surgical instrument end effector having integral FBGs.

FIG. 8 is an illustrative cross-sectional side view of a third embodiment of a surgical instrument end effector 802 having first and second integral FBGs 804, 806. The end effector 802 depends from a distal end portion of a surgical instrument shaft 26. The end effector 802 includes a center cantilever beam 808 disposed between first and second force-sensing cantilever beams 874, 876. In some embodiments, the center cantilever beam 808 and the first and second force sensing cantilever beams 874, 876 depend from and are integrally formed with a support base member 816. In some embodiments, the support base member 816 includes a pulley 852 that is rotatably mounted to at the a distal end of a surgical instrument shaft 26 for rotation about a pivot axis 818. From the discussion above, a person skilled in the art will understand the use of a clevis (not shown) and wires to control rotation of the pulley 752.

The center cantilever beam 808 includes a center cantilever beam proximal portion 812 integrally secured to the support pulley 852, a center cantilever beam distal portion 820 that includes a working surface 824 and includes a center cantilever beam shoulder portion 830 integrally secured between them. The center cantilever beam proximal 812 is thinner than the center cantilever beam distal portion 820 so as to allow more flexible bending of the center cantilever beam 808 in response to bending forces imparted to the distal end portion 820 The center cantilever beam shoulder portion 830 includes first and second opposite facing shoulder surfaces 878, 880 upstand from the shoulder portion 830 in opposite directions from each other. The first shoulder surface 878 upstands from the shoulder portion 830 in a direction toward the first force-sensing cantilever beam 874 so as to be spaced from the first force-sensing cantilever beam 874 by a small enough distance that a force imparted to the center cantilever beam distal portion 820 that causes a bending of the center cantilever beam proximal portion 812 in a first direction (e.g., counter-clockwise in the drawing), toward the first force-sensing cantilever beam 874, may cause the first shoulder surface 878 to make flexible bending contact and impart a force upon the first force-sensing cantilever beam 874. Similarly, the second shoulder surface 880 upstands from the shoulder portion 830 in a direction toward the second force-sensing cantilever beam 876 so as to be so as to be spaced from the second force-sensing cantilever beam 876 by a small enough distance that a force imparted to the center cantilever beam distal portion 820 that causes a bending of the center cantilever beam proximal portion 812 in a second direction (e.g., clockwise in the drawing), toward the second force-sensing cantilever beam 876, may cause the second shoulder surface 880 to make flexible bending contact and impart a force upon the second force-sensing cantilever beam 876.

The first force-sensing cantilever beam 874 defines a first channel 890, which in some embodiments includes a circular cross-section bore hole. A portion of a first optical fiber 892 having the first FBGs 804 formed thereon is disposed within the first channel 890. The second force-sensing cantilever beam 876 defines a second channel 894, which in some embodiments includes circular cross-section bore hole. A portion of a second optical fiber 896 having the second FBGs 806 formed thereon is disposed within the second channel 894.

During a surgical procedure, for example, a rotational position of the base pulley 852 and the center cantilever beam 808 and the first and second force-sensing cantilever beams 874, 876 may be fixed at the distal end of the shaft 26 while a surgeon manipulates the center cantilever beam working face surface 824 to impart a force $F_{C1}$ upon anatomical tissue 828. The center cantilever beam 808 has a longer longitudinal dimension than the first and second force-sensing beams 874, 876, and therefore, the center cantilever beam 808 can directly contact tissue that the first and second force-sensing beams 874, 876 cannot reach. A tissue counter-force $F_{C2}$ imparted to the working face surface 824 of the center cantilever beam distal portion 820 may cause the cantilever beam proximal portion 812 to bend in a direction toward the second force-sensing cantilever beam 876 such that the second shoulder surface 880 contacts and imparts a force $F_{S2}$ upon the second force-sensing cantilever beam 874, for example. No force is imparted to the second force-sensing beam 876, in this example, while the second shoulder surface 880 contacts and imparts the force $F_{S2}$ to the second force-sensing cantilever beam 876.

In accordance with some embodiments, the force $F_{S2}$ imparted by the second shoulder surface 880 upon the second force-sensing cantilever 876 beam may impart a strain to the second FBGs 806 causing a shift in the light wavelength reflected by the second FBGs 806. However, there is no shift in the light wavelength reflected by the first FBGs 804 while the second shoulder surface 880 contacts the second force-sensing cantilever beam 876. Thus the light wavelength reflected by the first FBGs 804, while the second shoulder surface 880 contacts the second force-sensing cantilever beam 876, can be used for temperature calibration of the second FBGs 806 to determine a temperature independent shift in reflected light wavelength of the second FBGs 806 caused by strain in the second force-sensing cantilever beam 876. A magnitude of the second force $F_{S2}$ may be determined based upon the temperature independent shift in reflected light wavelength of the second FBGs 806. Persons skilled in the art will appreciate that a force imparted to the first force-sensing cantilever beam 874 by the first shoulder surface 878 may result in a similar shift in the wavelength reflected by the first FBGs 804, which may be calibrated for temperature based upon the light wavelength reflected by the second FBGs 806, and will not therefore, be further explained herein.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the disclosure should be limited only by the following claims, and it is appropriate that the claims be construed broadly and in a manner consistent with the scope of the embodiments disclosed herein. The above description is presented to enable any person skilled in the art to create and use a wire rope with enhanced wire wrap. Various modifications to the embodiments will be readily apparent to those skilled in the art, and the generic principles defined herein may be applied to other embodiments and applications without departing from the spirit and scope of the invention. In the preceding description, numerous details are set forth for the purpose of explanation. However, one of ordinary skill in the art will realize that the invention might be practiced without the use of these specific details. In other instances, well-known processes are shown in block diagram form in order not to obscure the description of the invention with unnecessary detail. Identical reference numerals may be used to represent different views of the same or similar item in different drawings. Thus, the foregoing description and drawings of embodiments in accordance with the present invention are merely illustrative of the principles of the invention. Therefore, it will be understood that various modifications can be made to the embodiments by those skilled in the art without departing from the spirit and scope of the invention, which is defined in the appended claims.

What is claimed is:

1. A surgical instrument comprising:
an elongated shaft that includes a proximal end and a distal end;
a cantilever beam disposed at the distal end of the shaft;
wherein the cantilever beam includes a proximal portion and a distal portion, wherein the cantilever beam includes a working face surface (working face) and an opposite facing back face surface (back face), wherein the cantilever beam defines a channel that includes a hole that extends within the proximal portion and within the distal portion;
an optical fiber that extends within the channel hole;
a first fiber Bragg grating (FBG) formed in a segment of the optical fiber within a portion of the channel hole defined in the proximal portion; and
a second FBG formed in a segment of the optical fiber within a portion of the channel hole defined in the distal portion;
wherein a thickness between the working face and the back face at the proximal portion is different from a thickness between the working face and the back face at the distal portion.

2. The surgical instrument of claim 1,
wherein the channel is offset from a neutral axis of the cantilever beam.

3. The surgical instrument of claim 1,
wherein the distal portion is thicker than the proximal portion.

4. The surgical instrument of claim 1,
wherein the proximal portion is thicker than the distal portion.

5. The surgical instrument of claim 1,
wherein the optical fiber extends within the elongated shaft.

6. The surgical instrument of claim 1,
wherein the channel provides an opening at the back face; and
wherein the optical fiber extends through the back face.

7. A surgical instrument comprising:
an elongated shaft that includes a proximal end and a distal end;
a cantilever beam disposed at the distal end of the shaft;
wherein the cantilever beam includes a proximal portion and a distal portion, wherein the cantilever beam defines a channel that extends within the proximal portion and within the distal portion;
an optical fiber that extends within the channel;
a first fiber Bragg grating (FBG) formed in a segment of the optical fiber within a portion of the channel defined in the proximal portion;
a second FBG formed in a segment of the optical fiber within a portion of the channel defined in the distal portion;
a pulley rotatably mounted at distal end of the shaft;
a wire extending within the shaft and wrapped about a portion of the pulley and secured to the pulley to impart rotation thereto;
wherein the proximal portion of the cantilever beam is fixedly secured to the pulley.

8. The surgical instrument of claim 1,
wherein the optical fiber extends within the elongated shaft;
wherein the channel provides an opening at the back face; and
wherein the optical fiber extends through the back face.

9. A surgical instrument comprising:
an elongated shaft that includes a proximal end and a distal end;
a cantilever beam disposed at the distal end of the shaft;
wherein the cantilever beam includes a proximal portion and a distal portion, wherein the cantilever beam defines a channel that extends within the proximal portion and within the distal portion;
an optical fiber that extends within the channel;
a first fiber Bragg grating (FBG) formed in a segment of the optical fiber within a portion of the channel defined in the proximal portion;
a second FBG formed in a segment of the optical fiber within a portion of the channel defined in the distal portion;
a pulley rotatably mounted at distal end of the shaft;
a wire extending within the shaft and wrapped about a portion of the pulley and secured to the pulley to impart rotation thereto;
wherein the proximal portion of the cantilever beam is fixedly secured to the pulley;
wherein the optical fiber extends within the elongated shaft;
wherein the cantilever beam includes a working face surface and a back face surface;
wherein the channel provides an opening at the back face surface; and
wherein the optical fiber extends through the back face surface.

10. The surgical instrument of claim 1,
wherein the thickness between of one the working face and the back face of the proximal portion and the working face and the back face of the distal portion is sufficiently smaller than the thickness between the other of the working face and the back face of the proximal portion and the working face and the back face of the distal portion that a force imparted to the working surface of the cantilever beam imparts a greater bending strain to one of the first FBG and the second FBG than to the other of the first FBG and the second FBG.

11. The surgical instrument of claim 10,
wherein the thickness between the working face and the back face of the proximal portion is sufficiently smaller than thickness between the working face and the back face of the distal portion that the force imparted to the working surface of the cantilever beam imparts a greater bending strain to the first FBG than to the second FBG.

12. The surgical instrument of claim 10,
wherein the thickness between the working face and the back face of the distal portion is sufficiently smaller than thickness between the working face and the back face of the proximal portion that the force imparted to the working surface of the cantilever beam imparts a greater bending strain to the second FBG than to the first FBG.

* * * * *

UNITED STATES PATENT AND TRADEMARK OFFICE
CERTIFICATE OF CORRECTION

PATENT NO. : 10,675,107 B2
APPLICATION NO. : 16/192475
DATED : June 9, 2020
INVENTOR(S) : Steger et al.

Page 1 of 1

It is certified that error appears in the above-identified patent and that said Letters Patent is hereby corrected as shown below:

In the Claims

In Column 12, Line 36, in Claim 10, delete "of one" and insert --one of-- therefor Signed and Sealed this
Twenty-fifth Day of August, 2020

Andrei Iancu
*Director of the United States Patent and Trademark Office*